United States Patent
Mendoza

(10) Patent No.: US 7,939,515 B2
(45) Date of Patent: May 10, 2011

(54) ADMINISTRATION OF FLUOCINOLONE ACETONIDE, TRETINOIN AND HYDROQUINONE CREAM IN MELASMA MAINTENANCE THERAPY

(75) Inventor: Ivonne Arellano Mendoza, Mexico D. F. (MX)

(73) Assignee: Galderma S.A., Cham (CH)

( * ) Notice: Subject to any disclaimer, the term of this patent is extended or adjusted under 35 U.S.C. 154(b) by 0 days.

(21) Appl. No.: 12/457,732

(22) Filed: Jun. 19, 2009

(65) Prior Publication Data

US 2010/0029601 A1 Feb. 4, 2010

Related U.S. Application Data

(63) Continuation of application No. PCT/EP2007/064269, filed on Dec. 19, 2007.

(60) Provisional application No. 60/875,529, filed on Dec. 19, 2006.

(51) Int. Cl.
*A61K 31/56* (2006.01)
*A61K 31/58* (2006.01)
*A61K 31/02* (2006.01)

(52) U.S. Cl. .......................... 514/171; 514/174; 514/743

(58) Field of Classification Search .................. 514/174, 514/171, 734
See application file for complete search history.

(56) References Cited

U.S. PATENT DOCUMENTS

2004/0037201 A1 2/2004 Sako et al.

OTHER PUBLICATIONS

Torok, American Journal of Clinical Dermatology, Jul. 2006; 7(4):223-230.*

Taylor et al., "Efficacy and Safety of a New Triple-Combination Agent for the Treatment of Facial Melasma," *Cutis, Therapeutics for the Clinician*, vol. 72, pp. 67-72, Jul. 2003, New Jersey.

Cook-Bolden, et al., "The Use of a Triple-Drug Combination Product and Procedures for the Treatment of Hyperpigmentary Disorders," *Cosmetic Dermatology*, vol. 18, No. 8, pp. 589-594, 2005, Knolls Pub. Group, New Jersey.

Cestari et al., Validation of a melasma quality of life questionnaire for Brazilian Portuguese language: the MelasQoL-BP study and improvement of QoL of melasma patients after triple combination therapy, *British Journal of Dermatology*, 2006 156 (suppl. 1), 13-20, British Association of Dermatologists, Britain.

Torok et al., "A Large 12-month Extension Study of an 8-week trial to Evaluate the Safety and Efficacy of Triple Combination (TC) Cream in Melasma Patients Previously Treated with TC Cream or One of Its Dyads," *Journal of Drugs in Dermatology*, Sep./Oct. 2005, vol. 4, Issue 5, pp. 592-597, New York.

Grimes et al., "Community-Based Trial of a Triple-Combination Agent for the Treatment of Facial Melasma," *Cutis, Therapeutics for the Clinician*, vol. 77, No. 3, Mar. 2006, pp. 177-184, New Jersey.

Guevara et al., Melasma treated with hydroquinone, tretinoin, and a fluorinated steroid, *International Journal of Dermatology*, 2001, vol. 40, No. 3, 210-215, Blackwell Science Ltd., US.

Katz et al., "Intermittant Corticosteroid Maintenance Treatment of Psoriasis: A Double-Blind Multicenter Trial of Augmented Betamethasone Dipropionate Ointment in a Pulse Dose Treatment Regimen," *Dermatologica* 1991:183:269-274, Karget AG, Basel.

International Search Report for corresponding PCT/EP/2007/064269, issued Mar. 25, 2008 in English.

International Preliminary Report on Patentability for corresponding PCT/EP2007/064269, issued Jun. 24, 2009, 9 pages in English.

* cited by examiner

*Primary Examiner* — San-ming Hui

(74) *Attorney, Agent, or Firm* — Buchanan, Ingersoll & Rooney, P.C.

(57) ABSTRACT

Topical application of a triple combination immixture of fluocinolone acetonide, tretinoin and hydroquinone is useful for the maintenance therapy of melasma to prevent hyperpigmentation recurrence or reduce the severity of the hyperpigmentation recurrence.

2 Claims, No Drawings

ADMINISTRATION OF FLUOCINOLONE ACETONIDE, TRETINOIN AND HYDROQUINONE CREAM IN MELASMA MAINTENANCE THERAPY

CROSS-REFERENCE TO PROVISIONAL/PCT APPLICATIONS

This application claims priority under 35 U.S.C. §119 of U.S. Provisional Application No. 60/875,529, filed Dec. 19, 2006, and is a continuation/national phase of PCT/EP 2007/064269, filed Dec. 19, 2007 and designating the United States (published in the English language on Jun. 26, 2008 as WO 2008/074848 A1), each hereby expressly incorporated by reference in its entirety and each assigned to the assignee hereof.

CROSS-REFERENCE TO RELATED APPLICATION

Copending U.S. patent application Ser. No. 12/457,731, filed concurrently herewith, hereby also expressly incorporated by reference and also assigned to the assignee hereof.

BACKGROUND OF THE INVENTION

Melasma is an acquired, symmetric, irregular hypermelanosis on sun-exposed areas of the face, commonly seen in Latin American women, particularly those with IV-V skin types (Javaheri S M, Handa S, Kaur I et al. Safety and efficacy of glycolic acid facial peel in Indian Women with melasma. *Int. J. Dermatol.*, 2001;40:354-357).

It is a very frequent disease, although its true incidence is unknown. Many factors have been implicated in the pathogenesis of melasma; however, the most important ones remain UV radiations, hereditary predisposition, and hormonal dysfunction (Mosher D B, Fitzpatrick T B, Ortonne J-P, Hori Y. Hypomelanoses and Hypermelanoses. In: Freedberg I M, Eisen A Z, Wolff K, et al, eds. *Fitzpatrick's Dermatology in General Medicine.*, Vol.1. New York, N.Y.: McGraw-Hill; 1999: 945-1017; Barankin B, Silver S G, Carruthera A. The skin in pregnancy. *J. Cut. Med. Surg.*, 2002; 6(3): 236-40).

Melasma has historically been difficult to treat and therapy remains a challenge for this chronic condition.

The principal rules of therapy must encompass: sun protection, inhibition of tyrosinase activity, removal of melanin, and destruction or disruption of melanin granules. Pandya and Guevara particularly recommend that patients should use sunscreens to protect the skin from UV-A and UV-B radiation and also from visible light to avoid formation of new melanin and immediate darkening of preformed melanin. Those who routinely use a sunscreen along with other treatment modalities do better than those who do not (Pandya A G et al. *Dermatol. Clin.*, 2000;18(1):91-98; Vasquez M. Sanchez .J L, The efficacy of a broad spectrum in the treatment of melasma Cutis 193;32:92-96).

Topical treatments are the mainstay (Mosher D B et al. In: Freedberg I M, Eisen A Z, Wolff K, et al, eds. *Fitzpatrick's Dermatology in General Medicine.*, Vol. 1. New York, N.Y.: McGraw-Hill; 1999: 945-1017; Pathak M A et al. *J. Am. Acad. Dermato.*, 1986;15:894-9; Giannotti B, Melli M C. *Clin. Drug Invest.*, 1995; 0(suppl2):57-64)) for the management of melasma and current approaches include hydroquinone, considered as the gold standard depigmenting agent and other molecules such as azelaic acid, tretinoin, alpha and beta hydroxy acids, and topical corticosteroids used as monotherapy or in various combinations (Giannotti B, Melli M C. *Clin. Drug Invest.*, 1995; 0(suppl2):57-64.; Kimbrough-Green C K, Griffiths CEM, Finkel L J et al. *Arch. Dermatol.*, 1994;130:727-33; Gano S E, Garcia R L. Cutis 1979;23:239-41; Kang W H, Hcun S C, Lee S. *J. Dermatol.*, 1998;25:87-596; Katsambas A, Antoniou C H. *J. Eur. Acad. Dermatol. Venereol*, 1995;4:217-23; Kligman A M, Willis I. *Arch Dermatol.*, 1975;1 11:40-8.)

Recently, a stable fixed combination cream containing fluocinolone acetonide (FA), plus hydroquinone (HQ), plus tretinoin (RA) was developed. Several studies have been performed, comparing this fixed combination to its three corresponding dyads of active ingredient (FA+HQ), (FA+RA), (HQ+RA). These studies demonstrated better efficacy of the triple combination (FA+HQ+RA) over each dyad, after a 8-week treatment (Taylor S, Torok H, Jones T, et al. *Cutis* 2003;72:67-72).

However, melasma being a relapsing disease, there is a real need to address how to maintain efficacy achieved after acute treatment. Five hundred and sixty nine subjects previously treated in the above mentioned studies have been included in a 12-month extension trial to evaluate the safety of the trio fixed combination (Torok H, et al. *J Drugs Dermatol.*, 2005 Sep-Oct;4(5):592-7). The results shown that the triple combination cream applied once daily over a long-term period is safe and tolerable. But skin atrophy is a primary concern with the long-term use of topical corticosteroids. However in the extension study mentioned only two cases of skin atrophy were reported. Both cases of skin atrophy were mild in nature and did not lead to discontinuation in the study. However, skin atrophy remains a frequent objection of clinicians to the long-term use of topical medications containing corticosteroids. For this reason, it is necessary to determine a maintenance therapy use of triple combination cream with such a good efficacy, good tolerance without side effects. This new regimen can also be more attractive to patients who no longer apply the product every day throughout the period of treatment.

It is stated that in addition to efficacy, the triple combination cream fulfills important requirements of a maintenance therapy which are efficacy with hyperpigmentation improvement, safety with a good tolerability.

SUMMARY OF THE INVENTION

Surprisingly, it has now been demonstrated that an immixture containing fluocinolone acetonide (FA), hydroquinone (HQ), and tretinoin (RA) as maintenance therapy is effective to prevent hyperpigmentation recurrence or reduce the severity of the hyperpigmentation recurrence for a time of treatment less than 12 months. Indeed, one skilled in the art could not have foreseen that the treatment with an immixture, which is preferentially a triple combination cream, containing fluocinolone acetonide (FA), hydroquinone (HQ), and tretinoin (RA) as maintenance therapy would delay the recurrence of hyperpigmentation and provide a continued benefit for 8 months maximum.

The present invention thus provides an effective method of treating melasma on a long term basis to prevent recurrence of hyperpigmentation or to control hyperpigmentation recurrence in 8 months maximum. The invention features a maximum 6-month maintenance therapy regimen with an immixture containing fluocinolone acetonide (FA), hydroquinone (HQ), and tretinoin (RA) after an initial daily treatment with an immixture containing fluocinolone acetonide (FA), hydroquinone (HQ), and tretinoin (RA) during maximum 8 weeks.

This invention more particularly features a maximum 6-month maintenance therapy regimen with a triple combination cream containing fluocinolone acetonide (FA), hydroquinone (HQ), and tretinoin (RA) after an initial daily treatment with a triple combination cream containing fluocinolone acetonide (FA), hydroquinone (HQ), and tretinoin (RA) during maximum 8 weeks.

By maintenance therapy is intended: chronic treatment, long term treatment, preventive treatment.

DETAILED DESCRIPTION OF BEST MODE AND SPECIFIC/PREFERRED EMBODIMENTS OF THE INVENTION

Generally, the present invention features a regimen for treating melasma in a patient which comprises first applying on affected facial areas once daily an immixture containing fluocinolone acetonide (FA), hydroquinone (HQ), and tretinoin (RA), for maximum 8 weeks (initial treatment phase); and thereafter applying topically of the same immixture cream 3 times a week during a first month, thereafter two times a week during a second month and thereafter once a week during a third, fourth, fifth and sixth month.

The present invention more particularly features a regimen for treating melasma in a patient which comprises first applying on affected facial areas once daily triple combination cream containing fluocinolone acetonide (FA), hydroquinone (HQ), and tretinoin (RA), for maximum 8 weeks (initial treatment phase); and thereafter applying topically of the same triple combination cream 3 times a week during a first month, thereafter two times a week during a second month and thereafter once a week during a third, fourth, fifth and sixth month.

The said immixture, or dermatological preparation, may comprise 0.001% to 0.5% fluocinolone acetonide, 0.5% to 10% hydroquinone, and 0.01% to 1% tretinoin by weight.

The said dermatological preparation may preferentially comprise fluocinolone acetonide 0.01%, hydroquinone 4% and 0.05% tretinoin by weight.

The said immixture, or dermatological composition, may be in the form of an aqueous gel, cream or lotion, and preferentially formulated as a cream.

The present invention features a maintenance treatment of melasma by an initial treatment with an immixture containing fluocinolone acetonide (FA), hydroquinone (HQ), and tretinoin (RA) once daily for maximum 8 weeks followed by topical application of the same immixture 3 times a week during a first month, thereafter two times a week during a second month and thereafter once a week during a third, fourth, fifth and sixth month.

The present invention more particularly features a maintenance treatment of melasma by an initial treatment with a triple combination cream containing fluocinolone acetonide (FA), hydroquinone (HQ), and tretinoin (RA) once daily for maximum 8 weeks followed by topical application of the same a triple combination cream 3 times a week during a first month, thereafter two times a week during a second month and thereafter once a week during a third, fourth, fifth and sixth month. The following details a study that clearly demonstrates the clinical benefit of maintenance therapy with triple combination cream containing fluocinolone acetonide (FA) 0.01%, hydroquinone (HQ) 4%, and tretinoin (RA) 0.05%.

A total of 300 subjects with moderate to severe melasma have been enrolled in a randomized, multi-center, investigator-blind, controlled study in different centers. The population to be studied includes male and female subjects of any race, aged 18 years or older, with a global melasma severity score of at least 2 on a scale from 0 (none) to 3 (severe).

During the Initial Treatment Phase, subjects have been evaluated at Baseline and at Weeks 2, 4, 6, and 8. The immixture or triple combination containing fluocinolone acetonide, tretinoine and hydroquinone is topically applied once daily at bedtime to the affected facial areas over a period of 8 weeks. At Week 8 (or before if melasma global severity score is 0), all subjects with a melasma global severity score graded at 0 or 1 are eligible for the Maintenance Phase, and are randomized in one of the two regimen groups. The first group applied the triple combination 3 times a week during a first month, thereafter two times a week during a second month and thereafter once a week during a third, fourth, fifth and sixth month. The subjects applied the immixture or triple combination at bedtime on the previously affected areas, as long as global severity score is below 2 (moderate) for a maximum of 24 weeks (6 months).

A sunscreen SPF 60 is applied, during both acute and Maintenance Phase, at least twice daily (morning and midday). In case sun exposure cannot be avoided, re-application is done every two hours.

The subjects are evaluated every 4 weeks during the Maintenance Phase.

Subjects previously enrolled in Initial Treatment Phase treatment and having a global severity score of:
  0 (none) if Maintenance Phase starts before the end of the 8-week treatment
  0 (none) or 1 (mild) if Maintenance Phase starts after the 8-week treatment.

Clinical evaluation of efficacy and safety has been done:
The primary efficacy criterion is the time to relapse during the Maintenance Phase.

The secondary efficacy criteria is:
global severity score of melasma (full scale)
MASI (Melasma Area and Severity Index) score (recorded from clinical examination at each visit)
Subject's static global assessment of melasma (performed at each visit)
Global severity score of melasma:
The investigator assesses the severity of the subject's melasma (disease severity) at each visit.
The global severity assessment is outlined in the following table:

| | | |
|---|---|---|
| None | 0 | Melasma lesions approximately equivalent to surrounding normal skin or with minimal residual hyperpigmentation |
| Mild | 1 | Slightly darker than the surrounding normal skin |
| Moderate | 2 | Moderately darker than the surrounding normal skin |
| Severe | 3 | Markedly darker than the surrounding normal skin |

The time to relapse is defined as the duration between Baseline of Maintenance Phase and the visit where the relapse occurs. The Melasma Relapse is derived from the global severity score. Any subject who was allowed to enter the Maintenance phase [(with a global severity score of 0 (before the end of the 8-week (Initial Treatment Phase) or a global severity score of 0 or 1 (at week 8)] and who is getting a global severity score of at least 2 during this Maintenance phase is defined as a relapse. This is further transformed in a dichotomized variable (no relapse=0 and relapse=1).

Melasma Area and Severity Index (MASI):
The investigator scores (using the scales below) the darkness, homogeneity and area of melasma for further calculation of Melasma Area and Severity Index (MASI).

| Darkness (D) Grading Scale | Homogeneity (H) Grading Scale | Area (A) Value |
|---|---|---|
| 0 = Absent | 0 = Minimal | 0 = no involvement |
| 1 = Slight | 1 = Slight | 1 = <10% |
| 2 = Mild | 2 = Mild | 2 = 10-29% |
| 3 = Marked | 3 = Marked | 3 = 30-49% |
| 4 = Severe | 4 = Maximum | 4 = 50-69% |
| | | 5 = 70-89% |
| | | 6 = 90-100% |

The study statistician calculates a computed MASI score at the end of the study.

MASI score is used to evaluate the degree of melasma. The MASI system was developed by Kimbrough-Green et al. (Kimbrough-Green C K, Griffiths C E M, Finkel L J et al. *Arch Dermatol.*, 1994;130:727-33) and calculated by the following equation:

$$MASI=0.3\ (DF+HF)\ AF+0.3\ (DMR+HMR)\ AMR+0.3\ (DML+HML)\ AML+0.1\ (DC+HC)\ AC$$

Where D is darkness, H is homogeneity, A is area, F is forehead, MR is right malar, ML is left malar, C is chin, and the values 0.3, 0.1=respective percentages of the total facial area.

Subject's Static Global Assessment.

A global assessment of melasma will be performed by the subject at each visit and graded using the following scoring tool:

| | |
|---|---|
| 0 | Completely clear, No evidence of hyperpigmentation |
| 1 | Only minor visual evidence of hyperpigmentation |
| 2 | Significant evidence of hyperpigmentation |

The Safety assessment is conducted for all subjects at each visit after enrollment in the study.

All clinical medical events, whether observed by the Investigator or reported by the subject and whether or not thought to be drug-related, is considered adverse events. An adverse event (AE) can be any unfavorable and/or unintended sign (including an abnormal laboratory finding), symptom, or disease temporally associated with the use of a medicinal (investigational) product, whether or not related to the medicinal (investigational) product.

The result is that triple combination is effective, in this regimen in maintaining the melasma improvement achieved with a previous treatment (12 months).

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A regimen for the maintenance therapy of melasma, which comprises topically applying onto the affected skin areas of an individual in need of such treatment, once daily for a maximum period of 8 weeks, a triple combination immixture comprising 0.01% fluocinolone acetonide, 4% hydroquinone and 0.05% tretinoin by weight, and continuing such topical application of said triple combination immixture thereafter for a maximum period of 6 months, at a rate of 3 times a week during a first month, thereafter 2 times a week during a second month and then once a week during a third, fourth, fifth and sixth month, the total length of time of said regimen being a maximum of 8 months.

2. The regimen as defined by claim 1, said triple combination immixture comprising a cream.

* * * * *